United States Patent [19]

Kitanishi et al.

[11] Patent Number: 4,971,805

[45] Date of Patent: Nov. 20, 1990

[54] SLOW-RELEASING GRANULES AND LONG ACTING MIXED GRANULES COMPRISING THE SAME

[75] Inventors: Yasuhisa Kitanishi, Hino; Hiroaki Taniguchi, Zama; Tsuyoshi Kochi, Hino, all of Japan

[73] Assignee: Teysan Pharmaceuticals Co., Ltd., Japan

[21] Appl. No.: 255,199

[22] Filed: Aug. 25, 1988

[30] Foreign Application Priority Data

Dec. 23, 1987 [WO] PCT Int'l Appl. ... PCT/JP87/01017

[51] Int. Cl.$^5$ ............................................... A61K 9/58
[52] U.S. Cl. ................................. 424/494; 424/458; 424/459; 424/462; 424/468; 424/480; 424/482; 424/495; 424/497
[58] Field of Search ............... 424/468, 462, 458, 459, 424/497, 494, 495, 480, 482

[56] References Cited

U.S. PATENT DOCUMENTS

| | | | |
|---|---|---|---|
| 2,410,417 | 11/1946 | Andersen | 424/462 X |
| 4,794,001 | 12/1988 | Mehta et al. | 424/458 |

FOREIGN PATENT DOCUMENTS

| | | | |
|---|---|---|---|
| 0077956 | 10/1982 | European Pat. Off. | |
| 0103991 | 3/1984 | European Pat. Off. | 424/462 |
| 0148811 | 1/1985 | European Pat. Off. | |
| 0210540 | 7/1986 | European Pat. Off. | |
| 2272639 | 12/1975 | France | |
| 2331375 | 6/1977 | France | |
| 1464192 | 2/1975 | United Kingdom | |
| 1560841 | 2/1976 | United Kingdom | |
| 2098867 | 12/1982 | United Kingdom | 424/462 |
| 2159715 | 12/1985 | United Kingdom | 424/462 |

*Primary Examiner*—Thurman K. Page
*Attorney, Agent, or Firm*—Sughrue, Mion, Zinn, Macpeak & Seas

[57] ABSTRACT

Slow-releasing granules which are characterized by coating the quick-releasing granules which comprise an active ingredient, polyvinyl pyrrolidone polymer and a disintegrator where the polymer distributes in high concentration on the surface area of the granules, with a polyacid enteric material to form a complex between the polyvinyl pyrrolidone polymer and the polyacid, and long lasting mixed granules which comprise the quick-releasing granules and the slow-releasing granules, thus showing increased bioavailability of the active ingredient and high stability sustained for a long period of time.

10 Claims, No Drawings

SLOW-RELEASING GRANULES AND LONG ACTING MIXED GRANULES COMPRISING THE SAME

FIELD OF THE ART

The present inventions relate to slow-releasing granules with good physical properties and long acting mixed granules comprising the same.

Particularly, the present inventions relate to slow-releasing granules which are characterized by coating quick-releasing granules comprising, as essential components, the active ingredient and a polyvinyl pyrrolidone polymer (abbreviated to PVP hereinafter) with a polyacid enteric material (abbreviated to PA hereinafter) to form a complex of the PVP polymer with the PA enteric material on their surface and relates to long acting mixed granules comprising the slow-releasing granules and quick-releasing granules, uncoated with an enteric material.

BACKGROUND OF THE ART

As long acting preparations, various kinds of so-called enteric preparations have been investigated and practically applied, in which a usual quick-releasing preparation is coated with a so-called enteric substance on its surface whereby the preparation can stably withstand the gastric acid juice without dissolution in the stomach, then is disintegrated and dissolved, as it comes into contact with the weak-alkaline digestive fluid in the intestinal tracts.

For example, at the first step, (a) cores are spray-coated with a powdery drug, together with a variety of excipients, binders and disintegrators, as the cores are rotated or (b) a mixture of the powdery drug, a variety of excipients, disintegrators and binders is kneaded with an evaporable solvent such as alcohol and extruded out of a perforated basket into cylindrical granules.

At the next step, the quick-releasing preparation is uniformly coated, e.g., by spraying a solution of an enteric substance on its surface to give a slow-releasing (enteric) preparation.

The quick-releasing and slow-releasing granules are combined at a specific ratio to give a mixed preparation and the product is orally administered. The technique that the target concentration of an active ingredient in blood is achieved by the quick-releasing component at the early stage, while, by the slow-releasing component at the later stage, has been successfully applied to such a field as antibiotics in practice (see Japanese Patent Specification Laid-open No. 52-139713 (1977)).

The conventional techniques, however, tend to form the coated films of uneven thickness, when the solution of an enteric material is applied. Thinner film areas are first dissolved and the digestive juice comes through the parts into the preparation to allow the contents, especially the disintegrators and the excipients, to swell, resulting in disintegration of the granules and quicker release of the active ingredient included than in the other granules not yet disintegrated.

Generally, most of the quick-releasing preparations to be coated with an enteric film are porous, because they are produced by binding a powder with a binder. Thus, when the preparation is sprayed with a coating solution, the solution irregularly penetrates the inside of the preparation, resulting in uneven and excessive coating in several cases.

In case that the preparation has defects such as cracks on the coating films in addition to the uneven coating thickness, disintegration of the granules and dissolution of the contents start at an abnormally early stage and the uniform and reproducible dissolution cannot be absolutely expected.

In conventional techniques, cracking sometimes takes place after long-term storage, even in case that no crack was observed just after the preparation was produced. They are presumably caused by humid and mechanical stress.

There is another problem, in conventional techniques, that the contents migrate into the enteric coating. Generally speaking, the contents, especially the pharmaceutically active ingredients, have low molecular weight and many of them migrate into the outer enteric coating at a relatively high rate.

The migration of active ingredients depends upon the materials of the enteric coating, the compatibility and affinity between the contents and the coating film. Such phenomena cause, as a result, weakened protection of the contents from the gastric juice by the enteric coating. Especially, when the migration changes with the passage of time, it acts, as a major cause, to fluctuate the bioavailability (abbreviated to BAV hereinafter) of a long acting preparation.

Further, another problem in the conventional techniques is low disintegrability of the slow-releasing preparation. In the case that the enteric coating is dissolved by the intestinal digestive juice and the contents (namely quick-releasing preparation) are not readily but gradually dissolved from the surface into the digestive juice, BAV of high reproducibility cannot be expected, even if the dissolution behavior and disintegrability of the enteric coating itself would be improved. In other words, reproducible BAV cannot be expected in such a preparation as the rate-determining step for the absorption from the intestinal tracts into the body is not in the dissolution of the enteric coating, but in the dissolution of the contents. Consequently, as stated above, it is desirable for reproducible BAV that the whole granules are readily disintegrated in a short time by the digestive juice, once the coating has been dissolved.

Thus, the contents of the slow-releasing granules (namely quick-releasing granules) need to include a powerful disintegrator, but systematic investigation has hardly been made on such a powerful disintegrator that can be included in the contents of quick-releasing granules coated with an enteric material.

The problems remaining in the conventional techniques, in other words, the problems to be solved by the present invention, are as follows:

(a) The enteric coating is uneven in its thickness and excessive coating tends to happen.

(b) The contents, especially the active ingredient, migrate out through the enteric coating, resulting in fluctuation of BAV.

(c) BAV considerably fluctuates, because the preparation is not readily disintegrated in a short time by the impregnating digestive juice, after the enteric coating has been dissolved off.

(d) The enteric coating has defects, for example, cracks in some cases.

Thus, the present inventors have made intense study in order to solve these problems completely and economically.

DISCLOSURE OF THE INVENTION

The present inventions relate to slow-releasing granules and to long-acting mixed granules comprising the slow-releasing granules and quick-releasing granules which do not have the enteric coating.

Namely, the first and the second inventions in the present inventions are:

(1) Slow-releasing granules which are characterized by comprising quick-releasing granules which comprise, as essential components, an active ingredient, polyvinyl pyrrolidone polymer and a disintegrator, and on the surface area of which said polyvinyl pyrrolidone polymer is distributed in high concentration, and coating the quick-releasing granules with a polyacid enteric material to form a complex between the polyvinyl pyrrolidone polymer and the polyacid enteric material on the surface area, and (2) Slow-releasing granules which are characterized by comprising quick-releasing granules which comprise, as essential components, an active ingredient, polyvinyl pyrrolidone polymer and a powerful disintegrator homogeneously, and coating the quick-releasing granules with a polyacid enteric material to form a complex between the polyvinyl pyrrolidone polymer and the polyacid enteric material on the surface area.

The third and fourth inventions are:

(3) Long acting mixed granules which are characterized by comprising
  (a) quick-releasing granules which comprise, as essential components, an active ingredient, polyvinyl pyrrolidone polymer and a disintegrator, and on the surface area of which said polyvinyl pyrrolidone polymer is distributed in high concentration, and
  (b) slow-releasing granules which have been prepared by coating a surface area of said quick-releasing granules with a polyacid enteric material to form a complex between the polyvinyl pyrrolidone polymer and the polyacid enteric material on the surface area, and (4) Long acting mixed granules which are characterized by comprising
  (a) quick-releasing granules which comprise, as essential components, an active ingredient, polyvinyl pyrrolidone polymer and a powerful disintegrator, and
  (b) slow-releasing granules which have been prepared by coating a surface of said quick-releasing granules with a polyacid enteric material to form a complex between the polyvinyl pyrrolidone polymer and the polyacid enteric material on the surface area.

The long acting mixed granules according to the present invention means a mixture which comprises the quick-releasing granules and the slow-releasing granules, thus keeping the blood concentration of the active ingredient high for hours.

The best embodiment of the present invention:

The quick-releasing granules which are used to prepare slow-releasing granules for the first and the second inventions in the present inventions commonly contain, as essential components, the active ingredient, a PVP polymer and a disintegrator.

In the quick-releasing granules which are used to prepare the slow-releasing granules according to the present inventions, it is indispensable that most of the PVP polymer be distributed on the surface area of the granules. Such granules are prepared by sprinkling a mixed fine powder containing the active ingredient, a variety of excipients and disintegrators over the cores, preferably spherical nuclei of sucrose (nonpareil), simultaneously spraying a solution of a binder such as a PVP polymer and increasing the amount of the PVP polymer at the final stage.

As a commonly used binder, are cited cellulose derivatives such as hydroxypropyl cellulose, hydroxypropyl methyl cellulose, ethyl cellulose, sodium salt of carboxymethyl cellulose, starch derivatives such as hydroxypropyl starch, oligosaccharides and PVP polymers. In the production of the preparation according to the present inventions, however, it is the most economical and efficient to use a PVP polymer as a binder from the beginning and spray the granules with a large amount of the PVP polymer as much as possible at the final stage. It is a matter of course, as one of the embodiments of the present inventions, that a binder other than PVP is used at the initial stage and only PVP is applied at the final stage of the granulation.

As a PVP polymer used here, are cited, for example, a variety of polyvinyl pyrrolidone homopolymers different in polymerization degrees manufactured by General Aniline and Film Company (US), BASF (Germany), PVP K-15, PVP K-30, PVP K-60, or PVP K-90. Especially, grades of high polymerization degree such as PVP K-60 or PVP K-90 are preferably employed. Furthermore, PVP-vinyl acetate copolymer or PVP-styrene copolymer can be also used.

Further, in the present invention, a disintegrator should be added to the quick-releasing granules to be coated with an enteric material. The disintegrator is, for example, low-substitution hydroxypropyl cellulose (manufactured by Shin-Etsu Chemical Company with about 5 to 16% by weight of hydroxypropyl groups content, and abbreviated to L-HPC), croscarmellose sodium (partially crosslinked sodium carboxymethylcellulose manufactured by Asahi Chemical Co. and called commercially AcDiSol), calcium carboxymethylcellulose, hydroxypropyl starch, fine crystal cellulose (Abicell: manufactured by Asahi Chemical Co.), PVPP (a partially crosslinked homopolymer of N-vinyl-2-pyrrolidone, manufactured by GAF Co. (US), called commercially Polyplasdone). These substances are used together with the pharmaceutically active ingredients, excipients (for example, lactose, sucrose, corn starch or the like) and mixed with a binder for binding these powders. L-HPC, AcDiSol and PVPP are preferably used, because they have powerful disintegrability. These disintegrators rapidly swell up several times the initial volume in a short time of a few minutes, when they contact with water, to disintegrate the shell therearound effectively. The content of the disintegrators is sufficiently about 1 to 10% in the quick-releasing granules.

In the quick-releasing granules which are used to prepare slow-releasing granules according to the second invention in the present inventions, the disintegrator, as one of the essential components, should be selected from the powerful disintegrators as will be mentioned below. As a powerful disintegrator, are preferably cited L-HPC, AcDiSol and PVPP from the disintegrators mentioned above.

These disintegrators hastily expand their own volume several times the initial one within a few minutes, when they come into contact with water, whereby they can effectively collapse shell therearound. It is enough for the quick-releasing granules to contain the disintegrator in a content of about 1 to 10%.

The quick-releasing granules are formed by admixing a binder to a mixture of the active ingredients, a variety of excipients and the above-stated disintegrator, and it is preferred to produce them by coating a core, especially nonpareil, with these powders, as being sprayed with the binder, because this process can give uniformly spherical granules.

As a binder, is essential a PVP polymer is used as stated above, and it may also be combined with another substance which is usually used as a binder such as hydroxypropyl cellulose.

Generally, the PVP polymer is sprayed upon the granules in the form of a solution in an organic solvent so that it is included in the granules in an amount of about 0.5 to 10%.

The PVP-polymer used here is, for example, a homopolymer such as PVP K-90 or or a copolymer thereof.

In the present inventions, the excipient is lactose, sucrose or corn starch, which has been used as an excipient usually.

The resultant quick-releasing granules have not yet been subjected to any treatment for prolonged action or enteric treatment and mean particulate or granular preparations which are formed in usual manners.

The slow-releasing granules according to the present inventions are produced by drying the quick-releasing granules thoroughly and coating them with an enteric material.

The enteric substances used in the present inventions are PA substances bearing many carboxyl groups in their molecules. Examples are methacrylic acid-ethyl acrylate copolymer [manufactured by Rhom-Farma Co. (West Germany), Eudragit® L-300D], methacrylic acid-methyl methacrylate copolymer (Eudragit® L or Eudragit®S), hydroxy propyl methyl cellulose phthalate (manufactured by Shin-Etsu Chemical Co., HP-50, HP-55, HP-55S), hydroxypropyl methyl cellulose acetate phthalate (manufactured by Shin-Etsu Chemical Co., AS-LG, AS-LF, AS-MG, AS-MF, AS-HG, AS-HF), carboxymethyl ethyl cellulose [manufactured by Freunt Industry Co. (Japan)], cellulose acetate phthalate, and vinyl methyl ether-maleic anhydride copolymer [manufactured by GAF Co. (US), AN-139, AN-169].

Preferably, Eudragit® L, Eudragit® S and HP-55 are employed, because they have high contents of carboxyl groups with high safety.

These substances are combined with a suitable plasticizer and a dispersant and coated on the quick-releasing granules. In general, they are dissolved in a solvent and the solution is applied by a known method such as spraying.

<Action>

In the present inventions, the first point is to improve uniformity of the coating layer, when the quick-releasing granules are coated with an enteric material. Usually, the quick-releasing granules are essentially very porous, because they are produced by granulating powders of individual components with a binder. Hence, there is very high possibility of large fluctuation in impregnation of the enteric coating solution into the granules. Further, the coating operation is usually carried out by laminating thin layers little by little repeatedly for more than 1 hour. Therefore, at the early stage, the coating layers once formed are dissolved again by the solvent in the coating solution which is repeatedly sprayed to cause coating fluctuation. Especially, in case that the substrate of the quick-releasing granules is not spherical, but, e.g., cylindrical, the closest attention should be paid to the formation of uniform coating all over the surface. Uneven coating is largely due to individual differences between operators.

The present inventors have made intense study on the measures to resolve these problems.

In the present inventions, it is indispensable that, in the first invention, an increased amount of the PVP polymer is allowed to distribute on the surface areas of the quick-releasing granules, while in the second invention, the PVP polymer is uniformly included in the quick-releasing granules and a PA substance bearing a large amount of carboxyl groups is used as an enteric material in both inventions.

It has been well known that PVP is a vinyl polymer bearing a number of pyrrolidone rings on its side chains and instantaneously reacts with a PA compound such as a polyacrylic acid copolymer or maleic anhydride copolymer, when they contact with each other, to form a complex insoluble in an organic solvent [see E. Benk, Chem. Ztg. 78, 41 (1954)].

The present inventors have noticed this phenomenon and made the following model experiment.

A solution of Eudragit® L in a propanol-methylene chloride mixed solution was added dropwise to another solution of PVP K-90 in the same mixed solvent and instantaneous formation of white gel was observed on the interface between both solutions. It was confirmed that the gel never dissolved again, even when the solvent was further added to the mixture.

Accordingly, when the quick-releasing granules are sprayed with a PA compound, similar gelling reactions take place on the surface area to form insoluble thin layers uniformly. The gel is not dissolved again, at the next step, by the PA coating solution to prevent locally deep impregnation of the coating solution, resulting in formation of extremely uniform coating layers.

In fact, one of the slow-releasing granules formed was cut into two halves and the section was observed with microscopic photographs and found to have a very uniform skin. For comparison, the quick-releasing granules not containing PVP at all were prepared and so-called enteric granules were produced by coating the granules with Eudragit® L-100, then their cross sections were observed using their microscopic photographs and found to have considerably deteriorated uniformity in film thickness.

The skin layers formed according to the present invention showed suppressed migration of the active ingredients, no formation of cracks during storage and very stable dissolution properties for a long period of time.

In the slow-releasing granules according to the first invention, the impregnation of the PA compound inside the granules is prevented by the PVP polymer which distributes on their surface area in a high concentration. The gel complex of the PA compound with the PVP polymer is not dissolved in an organic solvent, but readily dissolved again by a weak aqueous alkali, thus the function as enteric coating is not affected at all.

This behavior is a very advantageous function for constituting the present inventions. Some techniques which form a coating film as an intermediary layer between the enteric skin layer and the quick-releasing granules have been already disclosed in the prior art for the same purpose as in the present inventions. Large amounts of intermediary layers, however, are needed for inhibiting the migration of active ingredients from the granules completely and it was extremely difficult to have another function to cause rapid disintegration in a very short time simultaneously.

The slow-releasing granules according to the first invention, especially the slow-releasing granules made from the quick-releasing granules containing L-HPC, AcDiSol or PVPP as a disintegrator, have such excellent disintegrability that one can observe with the naked eye that they disintegrate just as bursting in a dissolution solution. The property can effectively exhibit its advantage, when it is combined with the enteric coating formed in according with the present inventions.

In the slow-releasing granules according to the second invention, the PA compound more readily and easily comes into the quick-releasing granules in comparison with the case in the first invention and the resultant gel complex becomes in a dried state. Therefore, a powerful disintegrator is more essential in order that the function as slow-releasing granules is fully developed with high reproducibility.

As stated above, L-HPC, AcDiSol and PVPP are suitably used as a powerful disintegrator. A variety of disintegrators which are used in usual preparations have been investigated and calcium carboxymethylcellulose (for example, manufactured by Gotoku Pharmaceutical Co. ECG 505) was found to have relatively good disintegrability in addition to the 3 chemicals stated above. But, the slow-releasing granules therefrom were cracked, when they were stored at room temperature for a long period of time. Thus, the substance cannot meet the purpose of present inventions.

On the contrary, the slow-releasing granules based on the quick-releasing granules containing L-HPC, AcDiSol or PVPP can keep the good properties without change with the passage of time for a long period of time. These compounds have very excellent disintegration power and the quick-releasing granules therefrom were observed with the naked eye to disintegrate just as bursting, when they were dropped in a dissolution solution.

The slow-releasing granules and the quick-releasing granules according to the present inventions are most preferably formed with a centrifugal coater into almost spherical granules, but not formed into cylindrical granules with an extruder.

The spherical granules enable very high uniformity of the enteric coating and a desired level of quality is stably attained independently from technical levels of operators for granulation. Further, granules are the most suitable form of preparations for long action, because they prevent the ubiquitous distribution in digestive tracts.

Moreover, in the present inventions, it is possible to prepare a mixed preparation of 3 or more kinds of granules by combining other slow-releasing granules which differ in releasing behaviors with the quick-releasing and the slow releasing granules. The third granule should be excellent in stability and reproducibility as in the first and second ones.

The pharmaceutical preparation techniques according to the present invention can be applied to any orally applicable drugs and is very useful for the drugs with high migration. The drugs to which the manufacturing technique according to the present invention is applied are, for example, antibiotics such as Cephalexin, Cephaloglycin, Cephradine, Cefadroxil, Ampicillin, Amoxicillin (AMPC), Cyclacillin, Cefaclor; Chemotherapeutic agents such as Norfloxacin, Ofloxacin, Enoxacin, Pipemidic acid, Piromidic acid; antipyretic, analgesic anti-inflammatory agents such as Fenbufen, Pranoprofen, Flurbiprofen; antihypertensive agents such as Pindolol, Prazosin hydrochloride, Meticran, Labetalol hydrochloride; antiallergic agents such as Tranilast; agents for circulatory organs such as Nifedipine, Nicardipine hydrochloride, Ifenprodil tartarate, Vinpocetin or Ticlodipine; agents for urinary and reproductive organs such as Flavoxate hydrochloride or antipodagric agents such as Benzbromarone or Allopurinol. The present invention, however, is not limited to these drugs.

The most economical process for producing the longacting mixed granules is to mix the quick-releasing granules, which have been used in making the slow-releasing granules, with the slow-releasing granules having enteric coating, but the quick-releasing granules may be prepared quite differently. The long-acting mixed granules according to the present inventions are composed of 10 to 90 parts, preferably 20 to 60 parts of the quick-releasing granules and 90 to 10 parts, preferably 80 to 40 parts, of the slow-releasing granules.

<Examples>

The present invention will be illustrated in more detail by the following examples and comparisons where, unless otherwise noted, parts means parts by weight and % means % by weight.

Control 1

PVP-90 (manufactured by GAF Co. (US)) was dissolved in an isopropanol-methylene chloride 1:1 weight ratio mixed solvent to form a solution of 1.5 % concentration. Then, a 7 % solution of Eudragit® L-100 (methacrylic acid-methyl methacrylate 1:1 (in molar ratio) copolymer) in the same mixed solvent was gradually added to the above PVP solution. Slight turbid gel was immediately formed on the boundary surface between both solutions. The whole solution was stirred with a glass rod and the whole solution became gelled. The gel did not return to a homogeneous solution, even when the mixed solvent was newly added.

Further, a 5 % solution of HP-55 (manufactured by Shin-Etsu Chemical Co.), as a PA polymer, in the same mixed solvent was added and quite the same phenomenon was observed.

Examples 1 to 3, Comparative examples 1 to 3

(Production of quick-releasing granules containing a powerful disintegrator and its dissolution into gastric juice)

Granular sugar with relatively uniform particle size 2 kg was placed in a centrifugal coater (CF-360 for laboratories, manufactured by Freunt Industry Co. (Japan). Then, corn starch was sprinkled over the sugar particles, as they were sprayed with 1% PVP K-90 aqueous solution under rotation of the coater to form spherical core particles (nonpareil). They were dried in hot air at 50° C. and sieved to classify the particle size. The nonpareil was almost spherical granules of about 650 μm in the average diameter.

Separately, a sprinkling powder containing 80 parts of amoxicillin(AMPC), one of the penicillin antibiotics, and 20 parts of corn starch was prepared.

Granulation was effected using the nonpareil as a core, sprinkling the above powder over the cores, as they were sprayed with a 1.5 % PVP K-90 solution in isopropanol. The granules were dried in hot air at 50° C. to remove the solvent whereby quick-releasing granules were produced. These granules were used as a control. The granules contained 470 mg (potency) every of AMPC per gram. The content of PVP K-90 was about 1%. The granules were examined on their dissolution behavior in gastric juice using simulated gastric juice (called the first juice hereinafter, pH=1.2) at 37° C. according to the dissolution test of Japanese Pharmacopoeia No. 10.

In the meantime, six kinds of disintegrators listed in Table 1 were added to the sprinkling powder to effect granulation as in the control (Examples 1 to 3 and Comparison 1 to 3) and their dissolution behavior was examined. The composition was the pharmaceutically active ingredient 80 parts, corn starch 15 parts and disintegrator 5 parts.

The times until the half and the whole of AMPC were dissolved were defined as $T_{50}$ and $T_{100}$ and they are given in Table 1.

TABLE 1

|  | Disintegrator | $T_{50}$ (min.) | $T_{100}$ (min.) |
|---|---|---|---|
| Control | None | 10 | 45 |
| Example 1 | L-HPC (LH-11) | 0.8 | 5 |
| Example 2 | Croscarmelos Na (AcDiSol) | 1 | 4 |
| Example 3 | PVPP (polyplasdone) | 0.9 | 5 |
| Compar. 1 | Hydroxypropyl-starch (HPS-11) | 5 | 10 |
| Compar. 2 | CMC-Ca (ECG 50%) | 2.5 | 7 |
| Compar. 3 | Abicell | 4 | 12 |

As shown in Table 1, the disintegrator-free granules (the control) needed very long time for disintegration and showed that the slow-releasing granules prepared therefrom cannot meet the object of the present invention. On the contrary, the granules containing disintegrators more rapidly disintegrated than the control, although there was a little difference among them. Especially, the granules according to the present invention (Examples 1 to 3) had less than 1 minute $T_{50}$ and disintegration started immediately after the granules were placed in the dissolution test solution and we could see the granules disintegrate just as popcorn bursts.

Examples 4 to 6 and Comparative examples 4 to 6

(Production of slow-releasing granules containing a powerful disintegrator and dissolution in the intestinal juice)

Six kinds of quick-releasing granules containing 5% disintegrators prepared in Examples 1 to 3 and Comparisons 1 to 3 were used in an amount of 2 kg and they were coated with an enteric layer in a CF-360 coater. As an enteric substance, there was used a 7% Eudragit ® L-100 solution in an isopropanolmethylene chloride 1:1 (weight ratio) mixed solvent. The Eudragit ® L-100 contained about 10% of a plasticizer.

All kinds of the granules were coated, until the enteric substance formed about a 20 μm-thick surface layer.

The granules were thoroughly dried in a hot-air type drier at 50° C. and sieved to give slow-releasing granules having almost equal particle sizes. The potency of AMPC was about 400 mg per every gram of the granules (Examples 4 to 6 and Comparative examples 4 to 6).

These slow-releasing granules were packed in pouches made of polyethylene-laminated aluminum film and subjected to a accelerated 6-month storage test, observing changes with the passage of time in a thermo-hygrostat at 40° C. and 75% relative humidity. Then, individual granules were examined on their dissolution in the simulated intestinal juice (called the second juice hereinafter, pH 6.8) at 37° C. according to the dissolution in the Japanese Pharmacopoeia No. 10.

As in the case of Example 1, the time in which half of the AMPC is dissolved ($T_{50}$ in minutes) was compared and the results are given in Table 2.

TABLE 2

|  | Disintegrator | $T_{50}$ before storage test | $T_{50}$ after storage test |
|---|---|---|---|
| Example 4 | L-HPC | 7–8 | 7–8 |
| Example 5 | AcDiSol | 6–9 | 7–10 |
| Example 6 | PVPP | 7–8 | 7–9 |
| Compar. 4 | Hydroxypropyl starch | 11–13 | 12–15 |
| Compar. 5 | CMC-Ca | 9–10 | 2–13 |
| Compar. 6 | Abicel | 12–15 | 15–22 |

Each data show the range of the results from 5-time measurements.

As shown in Table 2, the slow-releasing granules containing L-HPC, Acdisol or PVPP as a disintegrator according to the present invention had adequately short and stabilized $T_{50}$ with fluctuation reduced.

In Comparison 5 containing CMC-Ca, a case showed abnormally quick dissolution, after the test on the change with the passage of time. The observation of the surface through a microscope revealed cracks on the enteric surface. Abicel (Comparison 6) made the dissolution very much poorer in comparison with the untreated quick-releasing granules and the change with time was great.

Examples 7 to 9 and Comparative examples 7 to 9

(Dissolution of slow-releasing granules containing powerful disintegrators in gastric juice)

The six kinds of slow-releasing granules prepared in Examples 4 to 6 and Comparisons 4 to 6 were observed on their dissolution in the first juice, before and after the storage. Granules were stirred in the first juice at 37° C. for 30 minutes and the dissolution of AMPC was determined. The results are given in Table 3. It shows, except the case of CMC-Ca, that the change with the passage of time is scarcely observed, although a slight leak through the enteric coating is noticed. In the slow-releasing granules with CMC-Ca (Comparative example 8), the resistance to the gastric juice very much lowered and a considerable leak of AMPC was observed through the enteric coating. This was thought, as described in Comparison 5, to be caused by the cracks in the enteric coating.

TABLE 3

| | Disintegrator | Leak of AMPC after agitation in first juice (%) | |
|---|---|---|---|
| | | Pre-storage | Post-storage |
| Example 7 | L-HPC | 2–4 | 2–4 |
| Example 8 | AcDiSol | 2–3 | 2–4 |
| Example 9 | PVPP | 2–3 | 2–4 |
| Compar. 7 | Hydroxypropyl starch | 2–3 | 2–3 |
| Compar. 8 | CMC-Ca | 4–10 | 15–23 |
| Compar. 9 | Abicel | 2–3 | 2–3 |

Note: the leak (%) was determined 5 times every test and the ranges of the data are shown in the table.

Example 10

(Thickness fluctuation of the enteric coating on the slow-releasing granules containing powerful disintegrators)

Five granules were sampled from the slow-releasing granules prepared in Example 4 (containing L-HPC as a disintegrator) and cut into halves. Then, the cross-sections were photographed through a microscope and the thickness of the enteric coating was measured. The measurement was conducted at 7 points every granule. The coating thickness was found to be 23.7 μm on the average and the standard deviation was 2.5 μm, which showed even thickness.

Quick-releasing granules were prepared as in Example 1, using hydroxypropyl cellulose (HPC-L, manufactured by Nippon Soda Co. (Japan)) instead of PVP K-90 as a binder. The quick-releasing granules contained about 1% of HPC-L.

The granules were coated, as in Example 4, with Eudragit ® L-100 to form slow-releasing granules. The 5 granules obtained were cut into halves and photographed through a microscope and the average thickness of the enteric coating and the standard deviation were measured. The average thickness was found to be 22.2 μm, but the standard deviation was 4.2 μm, which showed less thickness eveness in comparison with Example 4.

Example 11

(Thickness fluctuation of the enteric coating on the slow-releasing granules containing powerful disintegrators)

Nonpareil prepared in Example 1 was used to form quick-releasing granules having the following composition:

| | |
|---|---|
| N-(3,4-dimethoxycinnamoyl) anthranilic acid (generic name: Tranilast) | 5 parts |
| corn starch | 57 parts |
| nonpareil | 36 parts |
| PVP K-90 | 2 parts |
| Total | 100 parts |

A mixture of the active ingredient and corn starch was thoroughly crushed with a hammer mill and granulation was conducted by sprinkling the powder over the cores, while a 3% PVP K-90 solution in isopropanol was sprayed carefully as in Example 1 in the CF-360 coater. The granules were thoroughly dried in a hot-air drier at 50° C.

After drying, the granules were put through sieves. Spherical granules passing through 12-mesh and not passing through 24-mesh screens were collected as quick-dissolving granules.

A part of corn starch was replaced with AcDiSol and granulation was conducted in a similar manner. The final composition of quick-dissolving granules was as follows:

| | |
|---|---|
| N-(3,4-dimethoxycinnamoyl) anthranilic acid (generic name: Tranilast) | 5 parts |
| corn starch | 52 parts |
| nonpareil | 36 parts |
| AcDiSol | 5 parts |
| PVP K-90 | 2 parts |
| Total | 100 parts |

Two kinds of quick-releasing granules were coated with a 6% Eudragit ® L-100 solution in an isopropanol-methylene chloride 1:1 mixed solvent on their surface in the CF-360 coater. The enteric material additionally included a small amount of dispersed plasticizer and light anhydrous silicic acid. Coating was effected at a constant feed, as the granules are allowed to rotate under rotation of the rotor at 120 rpm. After completion of the coating, the solvent was thoroughly removed in a hot-air drier at 50° C. and the granules were sifted by using 12-mesh and 24-mesh screens Thus, thickness of the coating was measured on these slow-releasing granules as in Example 10 and both of them were found to have 25-μm thickness on the average and 2.4-μm standard deviation, which means extremely even coating.

Further, these granules were subjected to a dissolution test in the second juice at pH 6.8 according to Japanese Pharmacopeia No. 10. The dissolution test was repeated to draw a graph of the dissolution curve and read $T_{50}$. The results are given in Table 4.

TABLE 4

| Samples | dissolution juice | pH | $T_{50}$ (min.) |
|---|---|---|---|
| slow-releasing granule free from AcDiSol | the second juice (Jap. Pharmaco.) | 6.8 | 7.1 |
| slow-releasing granule | the second juice (Jap. Pharmaco.) | 6.8 | 5.6 |

The granules containing AcDiSol showed about a 1.5-minute shortening in $T_{50}$ compared with the AcDiSol-free granules.

Example 12

(Production of slow-releasing granules in which PVP polymer distributes on the surface of the quick-releasing granules in increased concentration)

Nonpareil obtained in Example 1 was used to form quick-releasing granules having the following composition by the following process:

| | |
|---|---|
| Norfloxacin | 20 parts |
| cornstarch | 32 parts |
| L-HPC | 8 parts |
| nonpareil | 36 parts |
| PVP K-90 | 4 parts |
| Total | 100 parts |

A mixture of Norfloxacin, corn starch and L-HPC in the above-cited proportion was finely crushed with a hammer mill. As in Example 1, nonpareil 1 kg was charged in the CF-360 coater and the fine powder was sprinkled over at a certain feed under blowing hot air at 50° C., as the granules were allowed to roll by rotating the rotor at 100 rpm. Simultaneously, a 3% PVP K-90 solution in isopropanol was sprayed through a nozzle at an increased feed rate with the passage of time. In other words, about 1/5 of the total volume was sprayed in the first 20 minutes, then about 1/5 in the second 20 minutes and the remaining 3/5, in the last 20 minutes. Especially, in the last 20 minutes, the amount of the binder sprayed tended to be excessive to the feed of the sprinkled powder and the rotor speed and the temperature of the hot air were raised so that the granules may not be blocked. The granules were dried, classified by sieving and 2.5 kg of the granules passing through 12-mesh screen but not passing through 24-mesh were collected.

The resultant quick-releasing granules 1 kg were placed in the CF-360 coater and coated with an enteric material under rotation of the rotor at 100 to 250 rpm, as slit air is blown in at a feed rate of 400 1/min at 45° C. The coating conditions were as follows.

A mixture of Eudragit® L-100 containing small amounts of fatty acid ester monoglyceride (a plasticizer) and light anhydrous silicic acid and Eudragit® S 100 at 3:1 weight ratio was dissolved in an isopropanol-methylene chloride 1:1 (in weight) mixed solvent to form a 6% solution. The quick-releasing granules under rotation were sprayed with the solution at a feed rate of 5-30 ml/min to give slow-releasing granules coated with 25 parts of the enteric coating composition.

For comparison, quick-releasing granules were prepared by the process where the spray rate of the PVP K-90 solution was not changed with time and coated with an enteric material as in the above-stated manner to form slow-releasing granules.

These 2 kinds of slow-releasing granules were packed in polyethylene-aluminum laminated pouches and examined for the change with the passage of time at 40° C. and 75% RH for 6 months. The 4 kinds of granules before and after the storage were stirred in the first juice (pH 1.2) at 37° C. and the dissolution of the active ingredient in the juice was determined after 60 minutes. The results are shown in Table 5.

TABLE 5

| Slow-releasing granules | Leak of Norfloxacin after agitation in the first juice (%) | |
|---|---|---|
| | pre-storage | post-storage |
| Example 12 | 5.3 | 7.2 |
| Comparison | 42.0 | 69.8 |

The granules in which the distribution of the binder became higher as getting nearer to the surface (Example 12) were overwhelmingly improved in their resistance to the first juice and showed reduced change with the passage of time.

Example 13

(Production of slow-releasing granules in which PVP polymer distributes on the surface of the quick-releasing granules in higher concentration than in the center and dissolution in gastric and intestinal juices)

Under quite the same conditions as in Example 1, almost spherical nonpareil of about 650 μm in average diameter were prepared.

Nonpareil (1 kg) was charged in the CF-360 coater and sprinkled with a powder containing the active ingredient and the excipient to form granules.

The sprinkling powder was composed of 80 parts of AMPC, 15 parts of corn starch and 5 parts of L-HPC in the finely powdered form.

The granulation was effected in accordance with the usual method, as a PVP K-90 solution in isopropanol was sprayed from a nozzle.

In this case, a 1% PVP K-90 solution was sprayed in the first 4/5 of the granulation, and a 3% solution was employed in the final 1/5 so that the distribution of PVP became higher as nearing to the surface. The quick-releasing granules were thoroughly dried and found to contain about 1.5% of PVP on the average.

The quick-releasing granules were coated with an enteric material containing Eudragit® L-100, a plasticizer and a light anhydrous silicic acid on their surface uniformly. The thickness of the enteric coating was about 20 μm. As in Example 12, another kind of slow-releasing granules was prepared, for comparison, using quick-releasing granules having no concentration gradient of PVP. The 2 kinds of granules were subjected to the dissolution test in the first juice (pH 1.2) and the second juice (pH 6.8). The results are shown in Table 6.

When they were stirred in the first juice for 60 minutes, leakage of the active ingredient was much more improved than in comparison. Further, the time needed for 50% dissolution of the active ingredient ($T_{50}$) in the second juice was largely shortened and sharp dissolution was observed. Thus, the granules prepared in this Example were proved excellent and satisfactory as slow-releasing granules.

TABLE 6

| Slow-releasing granules | Leakage of AMPC in the 1st juice for 60 min. | $T_{50}$ in the second juice |
|---|---|---|
| Example 13 | 2-3% | 3-5 minutes |
| Comparison | 7-9% | 10-12 minutes |

Note 1: Both of them contained 400 mg (potency) of AMPC every gram of granules.
Note 2: The data showed the ranges of the values observed 5 times, respectively.

Example 14

(Measurement of thickness fluctuation in the enteric coating of the slow-releasing granules in which PVP polymer distributes higher near the surface)

(No. 1): slow-releasing granules prepared in Example 13

(No. 2): slow-releasing granules prepared as a comparison in Example 13

(No. 3): slow-releasing granules prepared, according to Example 1, by coating quick-releasing granules containing hydroxypropyl cellulose (HPC-L, manufactured by Nippon Soda Co. (Japan)) as a binder instead of PVP K-90, with Eudragit® L-100

Each of 5 granules were sampled from the 3 kinds of slow-releasing granules, cut into halves and photographed through a microscope to measure the thickness of the enteric coating at 7 points every granule.

The average values and the fluctuations (standard deviations) are given in Table 7.

TABLE 7

| Granules No. | Average thickness (μm) | Standard deviation (μm) |
|---|---|---|
| 1 | 24.2 | 1.4 |
| 2 | 23.7 | 2.5 |
| 3 | 22.2 | 4.2 |

The results showed that the coating thickness of the No. 1 granules was very uniform.

Example 15

(Thickness fluctuation of the enteric coating of the slow-releasing granules in which PVP polymer distributed high near the surface and dissolution in intestinal juice)

The quick-releasing granules prepared in Example 2 (containing croscarmellose sodium as a disintegrator) were used to make granules precoated with several kinds of water-soluble polymers, respectively. The granules before coating were collected by removing the granules remaining on a 14-mesh screen and passing through a 24-mesh screen.

The conditions for precoating are summarized in Table 8.

TABLE 8

| Granule No. | Polymers | Coating weight based on the quick-releasing granules (%) | Coater |
|---|---|---|---|
| 1 | None (control) | 0 | — |
| 2 | PVP K-90 | 0.5 | CF-360 |
| 3 | PVP K-90 | 1.5 | " |
| 4 | PVP K-90 | 2.5 | " |
| 5 | TC-5 (R) (comparison) | 1.5 | 2 |

Note (1): both of PVP K-90 and TC-5(R) were dissolved in a ethylene chloride-isopropanol 1:1 (in volume) mixed solution and a 2% solution was sprayed.
Note (2): TC-5 (R) is hydroxypropyl methyl cellulose manufactured by Shin-Etsu Chemical Co. (Japan).

In other words, PVP K-90 as an agent for binding the active ingredient and the excipient evenly distributes in the part of the sprinkled powder in the No. 2 quick-releasing granules (where the amount of PVP K-90 is about 0.5% based on the granules) and the polymer is coated in different thickness in the quick-releasing granules in No. 3 and No. 4. Further, the quick-releasing granules in No. 5 were coated, instead of with PVP K-90, with hydroxypropyl methyl cellulose which cannot form any complex with a PA enteric material to form granules for comparison.

The precoated granules were thoroughly dried in a hot-air drier at 40° C.

The resultant quick-releasing granules (1 kg) were charged in the CF-360 coater and coated with an enteric material containing Eduragit® L-100, small amounts of a plasticizer (fatty acid ester monoglyceride) and light anhydrous silicic acid as in Example 2. Then, the organic solvents were thoroughly removed in a vacuum drier at 40° C.

The amount of the enteric coating was about 15% based on the dry weight and the thickness was about 20 μm. Further, all kinds of the slow-releasing granules contained about 400 mg (potency) of Amoxicillin every per gram.

Then, the granules of from No. 1 to No. 5 were placed in the second juice (pH 6.8) at 37° C. as in Example 13 and the juice was sampled under stirring with the passage of time to determine the dissolution of Amoxicillin. $T_{50}$ was read from the graph of the leakage. The results are given in Table 9.

TABLE 9

| Slow-releasing granules | $T_{50}$ in the second juice in min. |
|---|---|
| No. 1 (control) | 10–12 |
| No. 2 | 9–10 |
| No. 3 | 3–4 |
| No. 4 | 8–9 |
| No. 5 (comparison) | 11–12 |

Note: the data show the range of the values observed 5 times in each group.

As the results show, the sharpest dissolution of the active ingredient was observed in about a 1.5% precoating (No. 3). A 0.5% precoating (No. 2) showed little improvement compared with the control (No. 1). Probably, 0.5% precoating was too small for improvement. On the contrary, 2.5% prohibited the dissolution action of the second juice. It is presumably due to too much application.

Further, the granules coated with TC-5 (R) which do not form a complex with PA (No. 5) were examined as a comparison and the dissolution was found to be quite the same as in the control (No. 1). It has been clearly known that the shortening of the dissolution time in simulated intestinal juice in vitro is practically reproduced in human bodies. Accordingly, extremely stabilized BAV can be obtained by using the granules according to the present invention. Especially, for the drugs whose absorption site is limited to only the duodenum and the upper part of the small intestine, a dissolution as rapid as possible on an increase of pH is essential to increase the bioavailability of the slow-releasing granules and give good long-acting mixed granules possessing high reproducibility of the BAV.

Example 16

(Mixed granules consisting of quick-releasing granules containing a powerful disintegrators and of slow-releasing granules in which PVP polymer is distributed in high concentration on the surface area of the quick-releasing granules)

The quick-releasing granules prepared in Example 2 (containing croscarmellose Na as a disintegrator) and the slow-releasing No. 3 granules in Example 15 were mixed so that the ratio of AMPC potency became 3.5 (in the quick granules): 6.5 (in the slow granules).

The mixed granules were given to 4 male adults after eating a light meal so that the potency of AMPC corresponds to 500 mg. After administration, blood sampling was continued every 1 hour for 12 hours and the serum concentration of the active ingredient was determined by the cylinder-plate assay. Bacillus subtilis ATCC 6633 was used as a test bacterium.

As a control, the same volunteers, after 1-week cessation, were given 1 capsule of conventional Amoxicillin preparation (potency, 250 mg), then 1 additional capsule after 6 hours (totally 500 mg). Blood was gathered every 1 hour for 12 hours and the serum concentration of AMPC was determined. The serum concentrations vs. time curves of the two groups were compared.

The effective serum concentration of AMPC to a variety of infectious diseases was assumed to be 1 μg/ml and the time when the concentration was maintained was read from the graphs. The granules according to the present invention continuously kept the level for 8.5 hours, while in the control capsule, the serum concentration dropped to almost zero until the second administration after 6 hours and the effective level was maintained for 3.2 hours in the first administration and for 3.8 hours in the second, totaling intermittent 7 hours.

Example 17

(Long-acting mixed granules consisting of the quick-releasing granules containing a powerful disintegrator and of the slow-releasing granules which were prepared by coating the quick-releasing granules with an enteric material)

Long-acting mixed granules were prepared by mixing the quick-releasing granules in Example 1 (containing L-HPC as a disintegrator) with the slow-releasing granules in Example 4 so that the ratio of Amoxicillin potency became 3 (in the former): 7 (in the latter) and the total potency reached 500 mg. The mixed granules were tested by orally giving them to 24 healthy male adult volunteers. In other words, the volunteers were separated into 2 groups of 12 persons and the BAV of the long-acting granules was compared with that of conventional Amoxicillin capsules as a control by the crossover method. As a parameter for BAV, the area under the serum concentration-time curve (AUC) was measured and the results are given in Table 10.

TABLE 10

|  | Administration | AUC ($\mu g \cdot hr/ml$) |
|---|---|---|
| Long-acting mixed granules in the present invention | 500 mg after eating a snack | 15.6 |
| Capsules (control) | 250 mg (1 capsule) twice in 6-hour interval | 14.4 |

Table 10 shows that the single dose of the granules according to the present invention gives almost the same AUC as in the twice dose of the capsules under the same administration conditions with very excellent prolonged action.

Then, these preparations were packaged in polyethylenealuminum foil laminated film and stored at room temperature for 36 months. The AUC was compared with that in the control in the same manner. The results are shown in Table 11.

TABLE 11

| Preparations | AUC ($\mu g \cdot hr/ml$) |
|---|---|
| Mixed granules according to the present invention | 17.3 |
| Capsules (control) | 15.5 |

Namely, the long-acting mixed granules according to the present invention perfectly sustain their effect, even after a 3-year storage and this fact proves that the granules are a very stable preparation.

Industrial applications

The present inventions relate to slow-releasing granules having a very uniform enteric coating without excessive impregnation of the enteric material into the quick-releasing granules and the long-acting mixed granules therefrom. A barrier layer is formed inside the enteric coating as an inevitable consequence to prevent the contents from migrating out to the surface. This barrier layer enables the granules to sustain extremely stabilized BAV for a long period of time and the powerful disintegrator in the quick-releasing granules ensures the quick dissolution of the active ingredient, when the enteric coating has been dissolved, resulting in excellent BAV.

Accordingly, the slow-releasing granules and the long-acting mixed granules according to the present inventions can be used as a pharmaceutical preparation for an active ingredient which is required to sustain a certain level of concentration in blood for hours.

We claim:

1. Enteric granules which are characterized by comprising gastric granules which comprise, as essential components, an active ingredient, polyvinyl pyrrolidone polymer and a disintegrator, and which have a surface area where said polyvinyl pyrrolidone polymer is distributed in high concentration, wherein the gastric granules are coated with a polymeric enteric material selected from the group consisting of polymers of methacrylic acid, cellulose and vinylmethylether-maleic anhydride copolymers to form a complex between the polyvinyl pyrrolidone polymer and the polymeric enteric material on said surface area.

2. Slow-releasing granules according to claim 1 wherein the disintegrator is a low-substituted hydroxypropyl ether of cellulose, partially crosslinked sodium carboxymethyl cellulose and/or N-vinyl-2-pyrrolidone polymer.

3. Mixed granules which are characterized by comprising
   (a) gastric granules which comprise, as essential components, an active ingredient, polyvinyl pyrrolidone polymer and a disintegrator, which have a surface area wherein said polyvinyl pyrrolidone polymer is distributed in high concentration, and
   (b) enteric granules which have been prepared by coating a surface of said gastric granules with a polymeric enteric material selected from the group consisting of polymers of methacrylic acid, cellulose and vinylmethylether-maleic anhydride copolymers to form a complex between the polyvinyl pyrrolidone polymer and the polymeric enteric material on the surface area.

4. Long-acting mixed granules according to claim 3, wherein the disintegrator is a low-substituted hydroxypropyl ether of cellulose, partially crosslinked sodium carboxymethyl cellulose and/or N-vinyl-2-pyrrolidone polymer.

5. Enteric granules as claimed in claim 1, wherein said polymeric enteric material bears a plurality of carboxy groups in the molecule thereof.

6. Enteric granules as claimed in claim 1, wherein said polymeric enteric polymer is a methacrylic acid-(meth)acrylate copolymer, cellulose (acetate) phthalate or a derivative thereof.

7. An enteric granule as claimed in claim 1, wherein said polymeric enteric polymer is a methacrylic acid-(meth)acrylate copolymer or hydroxy propyl methyl cellulose phthalate.

8. Mixed granules as claimed in claim 3, wherein said polymeric enteric material bears a plurality of carboxy groups in the molecule thereof.

9. Mixed granules as claimed in claim 3, wherein said polymeric enteric polymer is a methacrylic acid-(meth)acrylate copolymer, cellulose (acetate) phthalate or a derivative thereof.

10. Mixed granules as claimed in claim 3, wherein said polymeric enteric polymer is a methacrylic acid-(meth)acrylate copolymer or hydroxy propyl methyl cellulose phthalate.